United States Patent
Ortiz

(10) Patent No.: US 7,779,845 B2
(45) Date of Patent: Aug. 24, 2010

(54) METHOD AND APPARATUS FOR ENDOSCOPICALLY PERFORMING GASTRIC REDUCTION SURGERY

(75) Inventor: Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 172 days.

(21) Appl. No.: 11/197,530

(22) Filed: Aug. 5, 2005

(65) Prior Publication Data

US 2007/0032702 A1 Feb. 8, 2007

(51) Int. Cl.
*A61B 19/00* (2006.01)

(52) U.S. Cl. .................. 128/898; 600/104; 600/201; 600/205

(58) Field of Classification Search .......... 600/104, 600/139, 141–142, 156, 201, 204, 205, 215, 600/219; 604/22, 118, 902, 909; 128/898
See application file for complete search history.

(56) References Cited

U.S. PATENT DOCUMENTS

| | | | |
|---|---|---|---|
| 4,676,778 A * | 6/1987 | Nelson, Jr. ............ | 604/45 |
| 5,080,663 A | 1/1992 | Mills et al. | |
| 5,376,101 A | 12/1994 | Green et al. | |
| 5,382,231 A * | 1/1995 | Shlain ............ | 128/898 |
| 5,437,681 A | 8/1995 | Meade et al. | |
| 5,462,558 A | 10/1995 | Kolesa et al. | |
| 5,514,159 A | 5/1996 | Matula et al. | |
| 5,540,705 A | 7/1996 | Meade et al. | |
| 5,571,119 A | 11/1996 | Atala | |
| 5,599,304 A * | 2/1997 | Shaari ............ | 604/94.01 |
| 5,709,693 A | 1/1998 | Taylor | |
| 5,713,910 A | 2/1998 | Gordon et al. | |
| 5,814,071 A | 9/1998 | McDevitt et al. | |
| 5,817,050 A * | 10/1998 | Klein ............ | 604/35 |
| 6,036,694 A | 3/2000 | Goble et al. | |
| 6,231,585 B1 * | 5/2001 | Takahashi et al. ........ | 606/191 |
| 6,346,111 B1 | 2/2002 | Gordon et al. | |
| 6,443,962 B1 | 9/2002 | Gaber | |
| 6,454,778 B2 | 9/2002 | Kortenbach | |
| 6,494,888 B1 | 12/2002 | Laufer et al. | |

(Continued)

FOREIGN PATENT DOCUMENTS

EP 1545336 6/2005

(Continued)

*Primary Examiner*—Linda C Dvorak
*Assistant Examiner*—Victoria W Chen
(74) *Attorney, Agent, or Firm*—Dean Garner

(57) ABSTRACT

An articulating endoscopic instrument is adapted for properly orienting the stomach for cutting and stapling in an efficient manner. The instrument includes a body member having a first end and a second end, a plurality of suction holes along the body member in fluid communication with a suction inlet at the first end of the body member for the creation of suction along the body member and an articulating joint positioned along the body member. A method for gastric reduction surgery is achieved by inserting an articulating endoscopic instrument within the stomach and articulating the articulating endoscopic instrument to generally assume the shape of the relaxed stomach, applying suction through the articulating endoscopic instrument to draw the stomach tissue into contact with the articulating endoscopic instrument, articulating the articulating endoscopic instrument to a desired orientation and completing the gastric reduction surgery.

4 Claims, 3 Drawing Sheets

U.S. PATENT DOCUMENTS

| | | |
|---|---|---|
| 6,506,196 B1 | 1/2003 | Laufer |
| 6,558,400 B2 | 5/2003 | Deem et al. |
| 6,656,194 B1 | 12/2003 | Gannoe et al. |
| 6,663,639 B1 | 12/2003 | Laufer et al. |
| 6,719,763 B2 | 4/2004 | Chung et al. |
| 6,719,764 B1 | 4/2004 | Gellman et al. |
| 6,746,460 B2 | 6/2004 | Gannoe et al. |
| 6,755,843 B2 | 6/2004 | Chung et al. |
| 6,773,440 B2 | 8/2004 | Gannoe et al. |
| 6,835,200 B2 | 12/2004 | Laufer et al. |
| 6,908,427 B2 | 6/2005 | Fleener et al. |
| 6,923,819 B2 | 8/2005 | Meade et al. |
| 2002/0107530 A1 | 8/2002 | Sauer et al. |
| 2003/0083674 A1 | 5/2003 | Gibbens, III |
| 2003/0171760 A1 | 9/2003 | Gambale |
| 2003/0181924 A1 | 9/2003 | Yamamoto et al. |
| 2003/0208209 A1* | 11/2003 | Gambale et al. ............ 606/144 |
| 2003/0216754 A1* | 11/2003 | Kraemer et al. ............ 606/142 |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0044354 A1 | 3/2004 | Gannoe et al. |
| 2004/0059350 A1 | 3/2004 | Gordon et al. |
| 2004/0082963 A1* | 4/2004 | Gannoe et al. ............ 606/153 |
| 2004/0088008 A1 | 5/2004 | Gannoe et al. |
| 2004/0122453 A1* | 6/2004 | Deem et al. ................ 606/151 |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0193190 A1* | 9/2004 | Liddicoat et al. ............ 606/153 |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens, III et al. |
| 2005/0021085 A1 | 1/2005 | Abrams et al. |
| 2005/0055038 A1* | 3/2005 | Kelleher et al. ............ 606/151 |
| 2005/0070931 A1 | 3/2005 | Li et al. |
| 2005/0075653 A1 | 4/2005 | Saadat et al. |
| 2005/0149072 A1* | 7/2005 | DeVries et al. ............. 606/153 |
| 2005/0203500 A1* | 9/2005 | Saadat et al. .................. 606/27 |
| 2005/0203547 A1* | 9/2005 | Weller et al. ................ 606/139 |
| 2005/0277975 A1* | 12/2005 | Saadat et al. ............... 606/191 |
| 2006/0106288 A1* | 5/2006 | Roth et al. .................. 600/204 |
| 2007/0005082 A1* | 1/2007 | Kraemer et al. ............ 606/153 |

FOREIGN PATENT DOCUMENTS

| | | |
|---|---|---|
| EP | 1569709 | 9/2005 |
| WO | WO00/61012 | 10/2000 |
| WO | WO01/10312 | 2/2001 |
| WO | WO01/66001 | 9/2001 |
| WO | WO02/35980 | 5/2002 |
| WO | WO03090631 | 11/2003 |
| WO | WO2004052594 | 6/2004 |
| WO | WO2004082487 | 9/2004 |

* cited by examiner

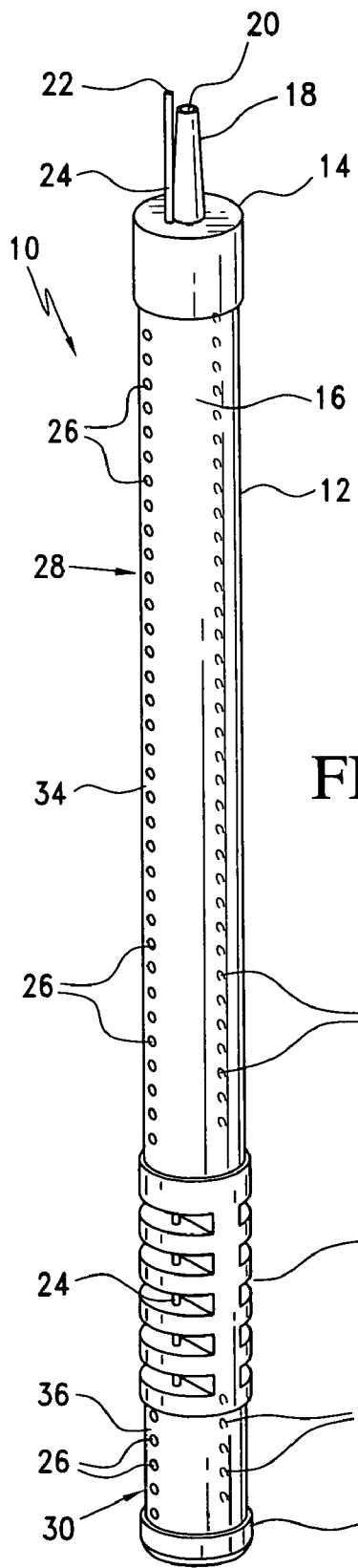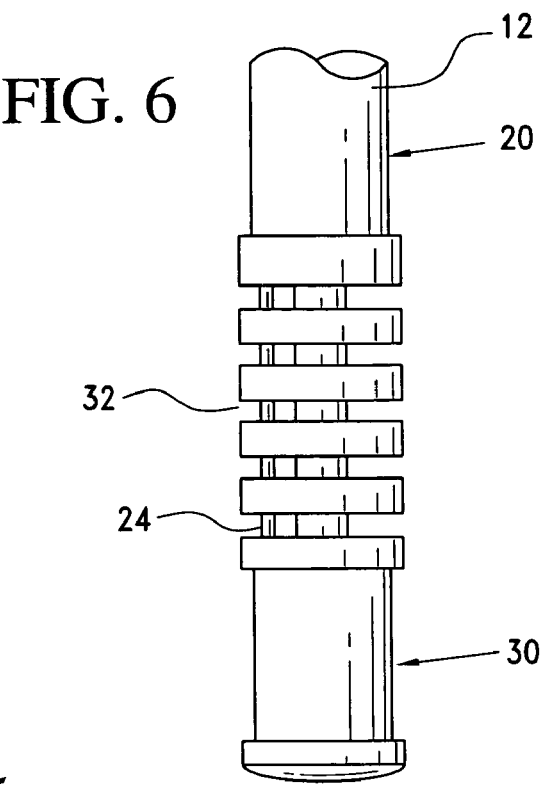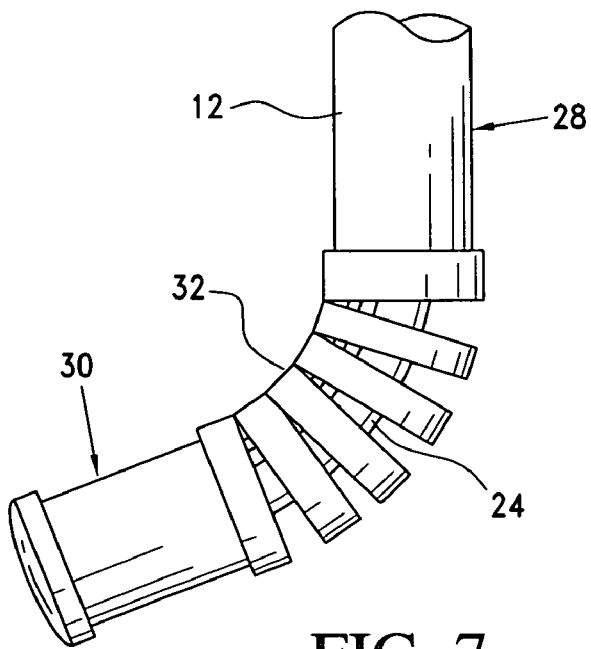

METHOD AND APPARATUS FOR ENDOSCOPICALLY PERFORMING GASTRIC REDUCTION SURGERY

BACKGROUND OF THE INVENTION

1. Field of the Invention

The present invention relates to gastric reduction surgery. More particularly, the invention relates to a method and apparatus for endoscopically performing gastric reduction surgery.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. One of the most commonly performed procedures is Roux-en-Y gastric bypass (RYGB). This procedure is highly complex and is utilized to treat people exhibiting morbid obesity. Even though this is a complex operation, greater than 100,000 procedures are performed annually in the United States alone. Other forms of bariatric surgery include Fobi pouch, bilio-pancreatic diversion, and gastroplastic or "stomach stapling". In addition, implantable devices are known which limit the passage of food through the stomach and affect satiety.

RYGB involves movement of the jejunum to a high position using a Roux-en-Y loop. The stomach is completely divided into two unequal portions (a smaller upper portion and a larger lower gastric pouch) using an automatic stapling device. The upper pouch typically measures less than about 1 ounce (or 20 cc), while the larger lower pouch remains generally intact and continues to secrete stomach juices flowing through the intestinal track.

A segment of the small intestine is then brought from the lower abdomen and joined with the upper pouch to form an anastomosis created through a half-inch opening, also called the stoma. This segment of the small intestine is called the "Roux loop" and carries the food from the upper pouch to the remainder of the intestines, where the food is digested. The remaining lower pouch, and the attached segment of duodenum, are then reconnected to form another anastomotic connection to the Roux loop at a location approximately 50 to 150 cm from the stoma, typically using a stapling instrument. It is at this connection that the digestive juices from the bypass stomach, pancreas, and liver, enter the jejunum and ileum to aid in the digestion of food. Due to the small size of the upper pouch, patients are forced to eat at a slower rate and are satiated much more quickly. This results in a reduction in caloric intake.

The conventional RYGB procedure requires a great deal of operative time. Because of the degree of invasiveness, postoperative recovery time can be quite lengthy and painful.

In view of the highly invasive nature of the current RYGB procedure, other less invasive procedures have been developed. The most common form of gastric reduction surgery involves the application of vertical staples along the stomach to create an appropriate pouch. This procedure is commonly performed laparoscopically and, as such, requires substantial preoperative, operative, postoperative resources.

Because of the degree of invasiveness, it is desirable to provide instruments and procedures that will assist in reducing the operative time and enhancing the overall procedure. The present invention provides an instrument and method for assisting in the performance of gastric reduction surgery with less invasive procedures resulting in reduced patient morbidity.

SUMMARY OF THE INVENTION

It is, therefore, an object of the present invention to provide an articulating endoscopic instrument adapted for properly orienting the stomach for cutting and stapling in an efficient manner. The instrument includes a body member having a first end and a second end, a plurality of suction holes along the body member in fluid communication with a suction inlet at the first end of the body member for the creation of suction along the body member and an articulating joint positioned along the body member.

It is also an object of the present invention to provide a method for gastric reduction surgery. The method is achieved by inserting an articulating endoscopic instrument within the stomach and articulating the articulating endoscopic instrument to generally assume the shape of the relaxed stomach, applying suction through the articulating endoscopic instrument to drawing the stomach tissue into contact with the articulating endoscopic instrument, articulating the articulating endoscopic instrument to a desired orientation and completing the gastric reduction surgery.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 5 is a perspective view of the present articulating endoscopic apparatus.

FIGS. 6 and 7 are detailed views of the distal end of the articulating endoscopic apparatus respectively shown in a substantially straight configuration and curved configuration.

DESCRIPTION OF THE PREFERRED EMBODIMENTS

Figure 1:
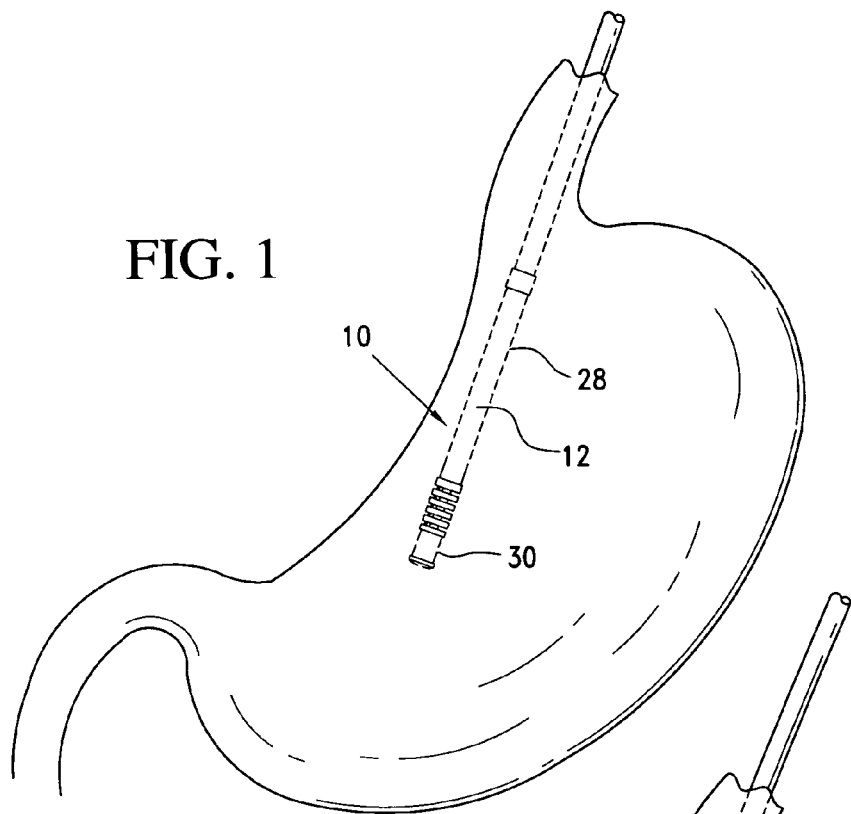
FIGS. 1 through 4 show the steps in utilizing the present articulating endoscopic apparatus.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

As those skilled in the art will certainly understand, RYGB involves movement of the jejunum to a high position using a retrocollic Roux-en-Y loop. The stomach is completely divided into two unequal portions (a smaller upper portion and a larger lower gastric pouch) using an automatic stapling device with the cut surface reinforced with additional sutures. The upper pouch typically measures less than about 1 ounce (or 20 cc), while the larger lower pouch remains generally intact and continues to secrete stomach juices flowing through the intestinal track.

A segment of the small intestine (just distal of the duodenum or proximal of the jejunum) is then brought from the lower abdomen and joined with the upper pouch to form an anastomosis created through a half-inch opening, also called the stoma. This segment of the small intestine is called the "Roux limb" and carries the food from the upper pouch to the remainder of the intestines, where the food is digested. The remaining lower pouch and the attached segment of duodenum are then reconnected to form another anastomotic connection to the Roux loop at a location approximately 50 to 150 cm from the stoma, typically using a stapling instrument. It is at this connection that the digestive juices from the bypass stomach, pancreas, and liver, enter the jejunum or ileum to aid in the digesting of food. Due to the small size of the upper pouch, patients are forced to eat at a slower rate and are satiated much more quickly. This results in a reduction in caloric intake.

As discussed above, the stomach is completely divided into two unequal portions using an automatic stapling device with the cut surface reinforced with additional sutures. However, because of the natural shape of the stomach and the desire that the smaller upper portion be curved, it is currently difficult to cut and staple the cut end of the smaller upper portion.

The present invention addresses this problem by providing an articulating endoscopic instrument 10 adapted for properly orienting the stomach for cutting and stapling the stomach in an efficient manner. With reference to FIGS. 5, 6 and 7, the instrument 10 generally includes a body member 12 having a first end 14 and a second end 16. The first end 14 includes a coupling structure 18 for attachment to the distal end of a proximally extending shaft. More particularly, the first end 14 includes a suction inlet 20 adapted for fluid communication with a suction line for the purpose of creating suction in a manner that will be described below in greater detail. The coupling structure 18 further includes a link member 22 for linking the articulation control cable 24 to the proximal end of the gastroscope for adjustment of the articulating endoscopic instrument 10 by the individual performing the surgery.

Between the first end 14 and the second end 16 of the body member 12 are the operating components of the present instrument 10. In particular, the instrument 10 includes a series of suction holes 26 extending along the length of the body member 12. The suction holes 26 are in fluid communication with the suction inlet 20 for the application of suction along the body member 12 in a manner discussed below in greater detail.

In accordance with a preferred embodiment of the present invention, the suction holes 26 are divided between the proximal end 28 of the body member 12 and the distal end 30 of the body member 12 with an articulation joint 32 positioned therebetween. As such, the suction holes 26 generally define a proximal suction section 34 and a distal suction section 36.

The articulation joint 32 is generally a flexible section along the length of the body member 12, which, under control of the articulation cable 24 is moved in a desired manner between a substantially straight configuration (see FIG. 6) and a curved configuration (see FIG. 7). In accordance with a preferred embodiment of the present invention, the articulation cable 24 is off center and therefore creates torque around a neutral axis when tensioned in a manner flexing the body member 12.

Figure 2:
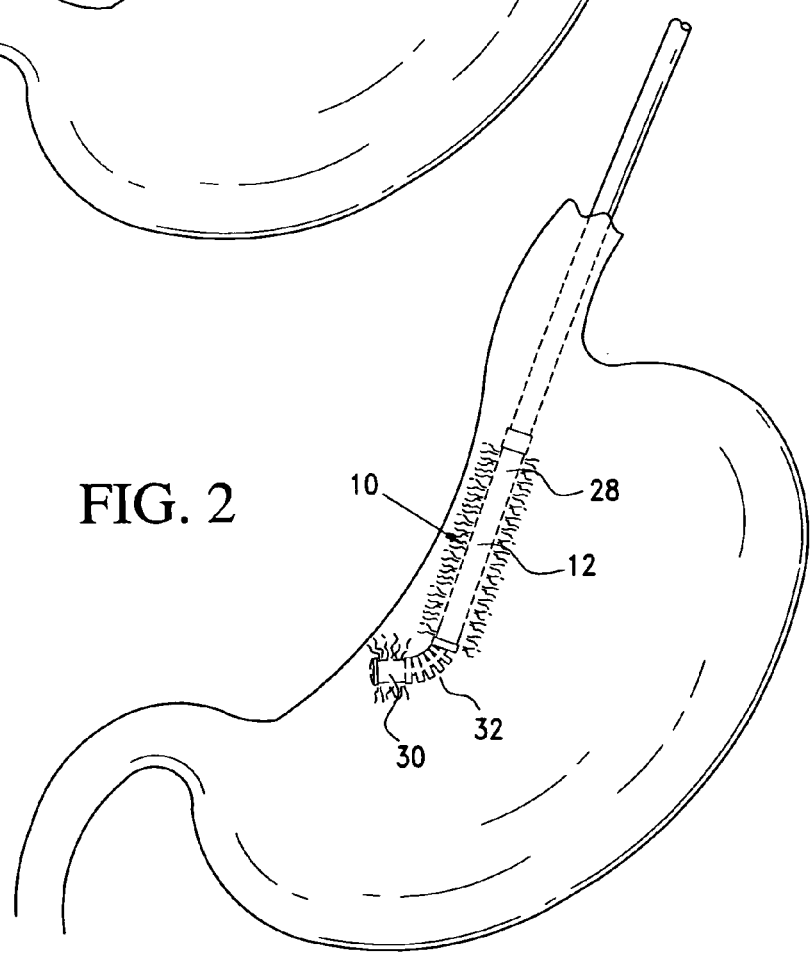
Figure 3:
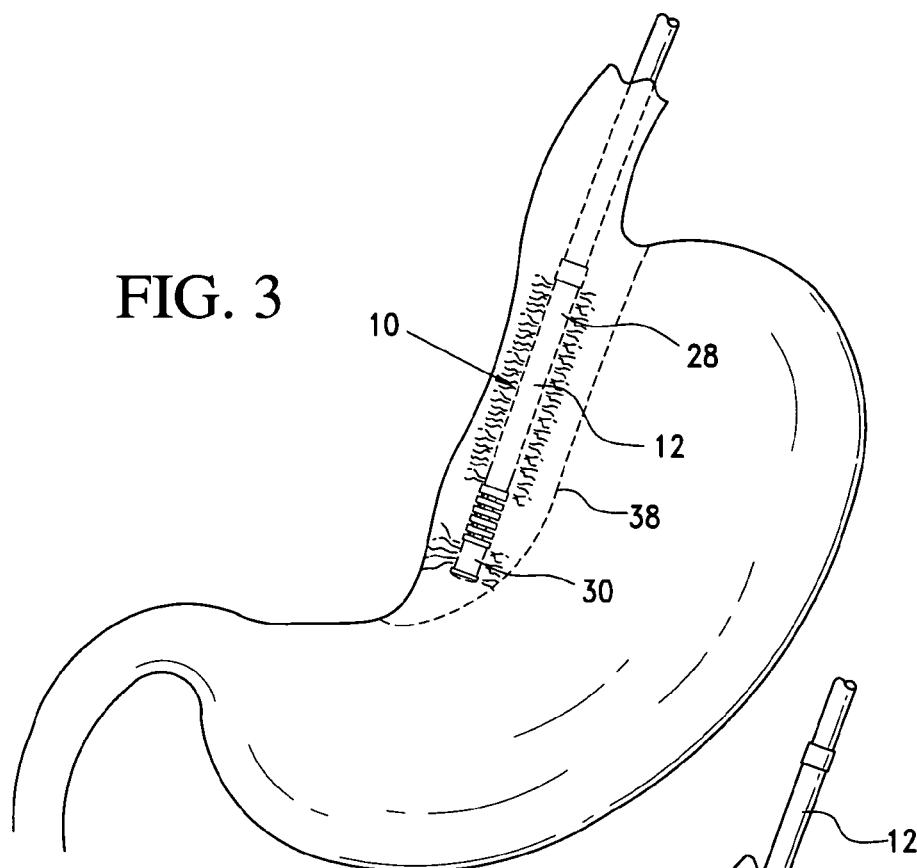
Figure 4:
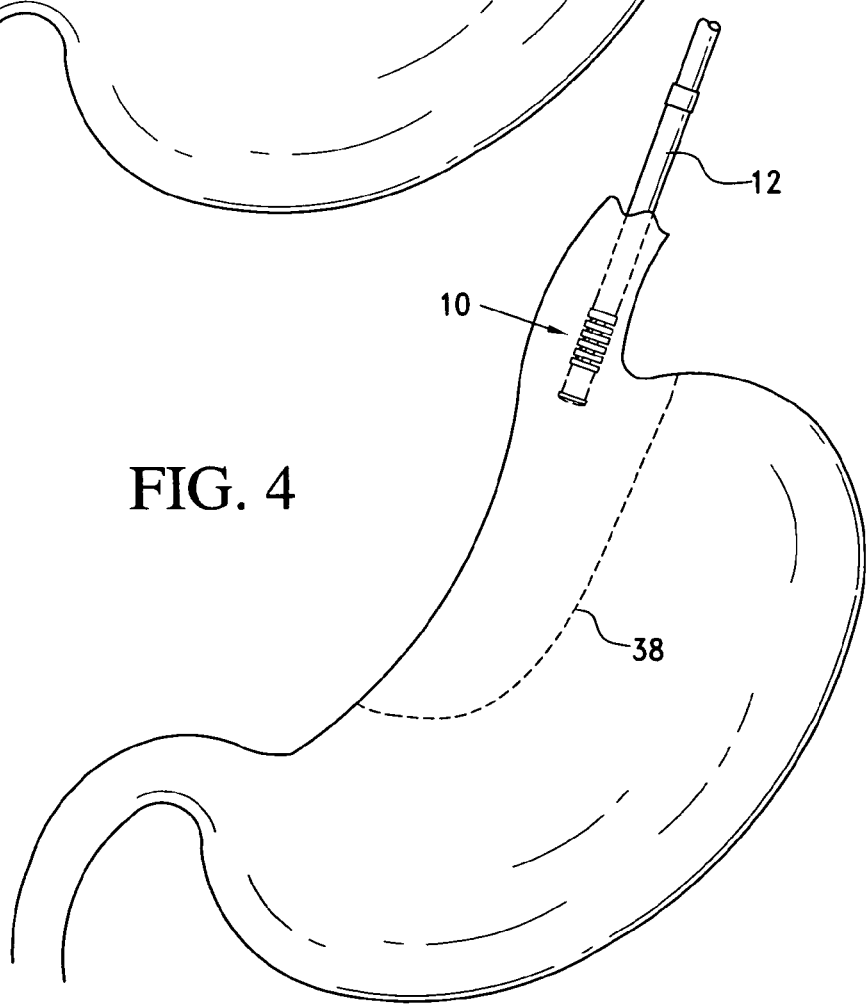

Generally, the articulating endoscopic instrument 10 uses suction and tissue traction to articulate the stomach tissue from its naturally curved shape (see FIGS. 1, 2 and 4) to a straightened shape (see FIG. 3) such that a straightened staple line 38 may be applied. The straightened staple line 38 is subsequently curved after the articulating endoscopic instrument 10 is removed and the stomach tissue is relaxed to its original configuration. The articulating endoscopic instrument 10 is generally inserted transorally and is articulated via the articulation cable 22 to assume a desired shaped, forcing the gastric pouch to a desired shape.

In practice, and in accordance with a preferred embodiment of the present invention, the articulating endoscopic instrument 10 is inserted into the stomach transorally (see FIG. 1) and is articulated to assume the shape of the gastric pouch. Thereafter, suction is applied drawing the stomach tissue into contact with the articulating endoscopic instrument 10 (see FIG. 2). Thereafter, the articulating endoscopic instrument 10 is straightened, providing an ideal staple line 38 for the application of staples and cutting of the stomach tissue (see FIG. 3).

Once the stomach is oriented in a predetermined and desirable straight configuration, a laparoscopic endocutter is fired along the axis of the manipulator as many times as are required to create the pouch for the RYGB procedure. More specifically, the endocutter is positioned alongside the straightened manipulator and fired to cut the stomach wall in a desired manner. As those skilled in the art will certainly appreciate, a variety of endocutters are known within the art and may be used in accordance with the present invention. Thereafter, the suction applied to the articulating endoscopic instrument 10 is released and the staple line 38 relaxes back to its curved orientation. The articulating endoscopic instrument is then removed and the RYGB procedure may then be completed (see FIG. 4).

The utilization of the present articulating endoscopic instrument and laparoscopic endocutter in accordance with the present invention and as described above, results in a stomach that is completely divided into two unequal portions (a smaller upper portion and a larger lower gastric pouch). In accordance with preferred application of the RYGB procedure, the upper pouch is typically formed such that it measures less than about one ounce, while the lower larger pouch remains generally intact and continues to secrete stomach juices following through the intestinal track.

As those skilled in the art will certainly appreciate, the present articulating endoscope and associated technique are particularly focused upon the creation of the smaller upper portion and the larger lower gastric pouch. Once these elements are formed, a segment of the small intestine (just distal of the duodenum or proximal of the jejunum) is brought from the lower abdomen and joined with the upper pouch to form an end-to-end anastomosis created through a half-inch opening, also called the stoma. The segment of the small intestine is called the Roux limb and carries food from the upper pouch to the remainder of the intestines, where the food is digested. The remaining lower pouch and the attached segment of the duodenum are then reconnected to form another anastomotic connection to the Roux limb at a location approximately 50 to 150 cm from the stoma, typically using a stapling instrument. It is at this connection that the digestive juices from the bypass stomach pancreas and liver enter the jejunum or ileum to aid in the digesting of food. Due to the small size of the upper pouch, patients are forced to eat at a slower rate and satiated much more quickly, thereby reducing the caloric intake.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for gastric reduction surgery, comprising the following steps:

inserting an articulating endoscopic instrument having a longitudinal axis within a stomach and articulating the articulating endoscopic instrument to a curved configuration generally assuming the shape of the relaxed stomach;

applying suction through a plurality of suction holes longitudinally formed along the articulating endoscopic instrument to draw the stomach tissue into contact with the articulating endoscopic instrument;

articulating the articulating endoscopic instrument from the curved configuration to a substantially straight configuration while the suction is applied to articulate the stomach tissue from its natural shape to a straightened shape; and completing the gastric reduction surgery, wherein the step of completing includes stapling and cutting the straightened stomach tissue along the longitudinal axis of the articulating endoscopic instrument.

2. The method according to claim 1, wherein the articulating endoscopic instrument comprises a body member having a first end and a second end, the first end of the body member including means for coupling to an elongated shaft; the plurality of suction holes along the body member being in fluid communication with a suction inlet at the first end of the body member for the creation of suction along the body member; and an articulating joint positioned along the body member.

3. The method according to claim 1, wherein the step of inserting is performed transorally.

4. The method according to claim 1, wherein the step of completing further includes performing a RYGB procedure.

* * * * *